(12) United States Patent
Fontana

(10) Patent No.: US 8,853,396 B2
(45) Date of Patent: Oct. 7, 2014

(54) METHODS FOR THE PREPARATION OF LAPATINIB AND THE SALTS THEREOF

(75) Inventor: Francesco Fontana, Alte di Montecchio Maggiore (IT)

(73) Assignee: F.I.S. Fabbrica Italiana Sintetici S.p.A., Montecchio Maggiore (VI) (IT)

( * ) Notice: Subject to any disclaimer, the term of this patent is extended or adjusted under 35 U.S.C. 154(b) by 8 days.

(21) Appl. No.: 13/414,752

(22) Filed: Mar. 8, 2012

(65) Prior Publication Data

US 2012/0245350 A1 Sep. 27, 2012

(30) Foreign Application Priority Data

Mar. 25, 2011 (IT) .............................. MI2011A0480

(51) Int. Cl.
*C07D 405/04* (2006.01)
*C07D 405/14* (2006.01)

(52) U.S. Cl.
CPC ............ *C07D 405/04* (2013.01); *C07D 405/14* (2013.01)
USPC ....................................................... 544/293

(58) Field of Classification Search
CPC .................................................... C07D 405/04
USPC ....................................................... 544/293
See application file for complete search history.

(56) References Cited

U.S. PATENT DOCUMENTS

| 7,157,466 B2 | 1/2007 | McClure |
| 2003/0220354 A1 | 11/2003 | McClure |
| 2013/0005971 A1 * | 1/2013 | Chen et al. .................... 544/287 |

FOREIGN PATENT DOCUMENTS

WO    WO 2011116634 A1 *  9/2011

OTHER PUBLICATIONS

"The Chemistry of the Halogens." Purdue University. Available from: < http://web.archive.org/web/20090414155348/http://chemed.chem.purdue.edu/genchem/topicreview/bp/ch10/group7.php >. Published online Apr. 14, 2009.*
Italian Search Report IO 22400 IT MI20110480—Jul. 12, 2011.

* cited by examiner

*Primary Examiner* — Andrew D Kosar
*Assistant Examiner* — John S Kenyon
(74) *Attorney, Agent, or Firm* — Robert E. Alderson, Jr.

(57) ABSTRACT

Methods for the synthesis of the pharmaceutically active ingredient Lapatinib and the salts thereof are provided. In particular, such methods utilize intermediates in which the hydroxyl function is protected by a tetrahydropyranyl group providing greater solubility of the intermediates in common organic solvents.

14 Claims, 1 Drawing Sheet

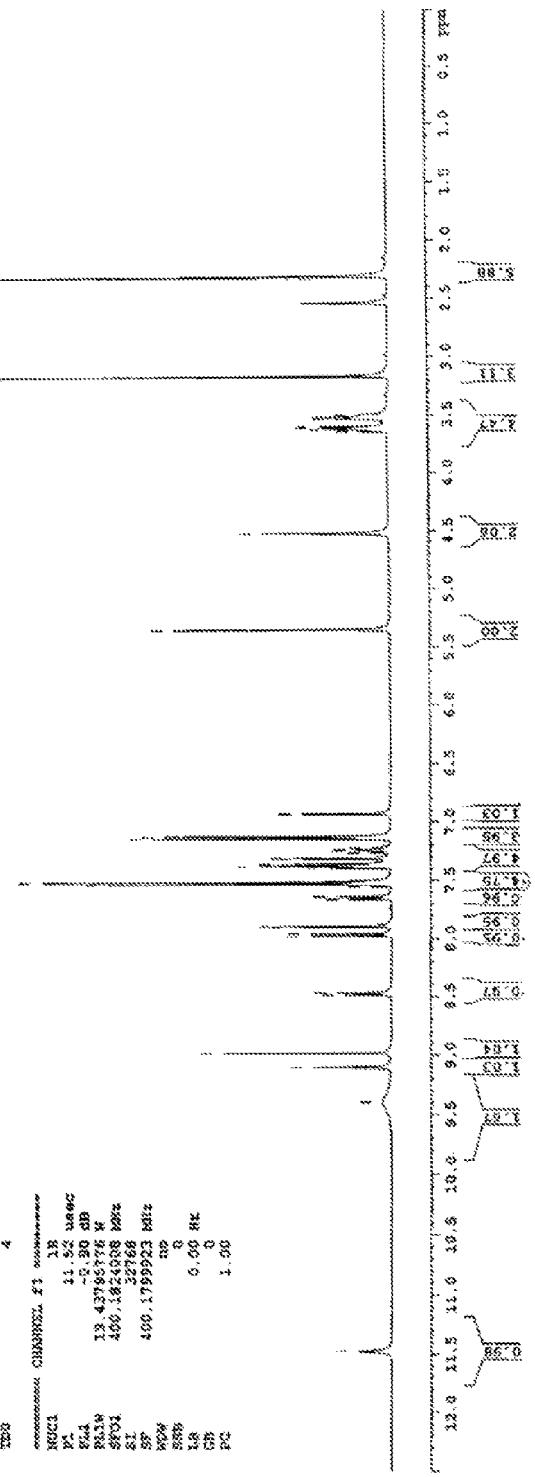

METHODS FOR THE PREPARATION OF LAPATINIB AND THE SALTS THEREOF

CROSS REFERENCE TO RELATED APPLICATION

This application claims priority to and benefit of Italian Patent Application No. MI2011A000480 filed Mar. 25 2011

FIELD OF THE INVENTION

The present invention relates to methods for the synthesis of the pharmaceutical active ingredient Lapatinib and salts thereof.

BACKGROUND OF THE INVENTION

Lapatinib is a pharmaceutical active ingredient used for the treatment of advanced metastatic lung cancer and it is currently available on the market under the name Tykerb® sold by GlaxoSmithKline (GSK).

According to manufacturer, Tykerb® contains Lapatinib as monohydrate ditosylate salt of formula (I-bis):

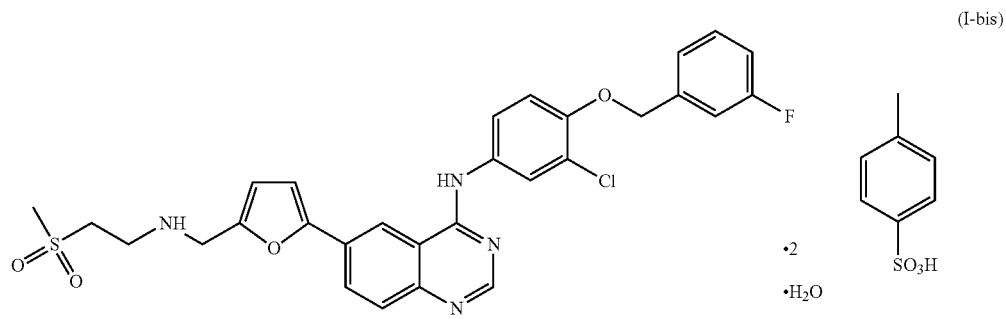 [SMILES: CS(=O)(=O)CCNCc1ccc(-c2ccc3ncnc(Nc4ccc(OCc5cccc(F)c5)c(Cl)c4)c3c2)o1 ; O ; Cc1ccc(S(=O)(=O)O)cc1]

(I-bis)

having the chemical name of N-{3-chloro-4-[(3-fluoro-benzyl)oxy]phenyl}-6-[5-({[2-(methylsulfonyl)ethyl]amino}methyl)furan-2-yl]quinazoline-4-amine bis(4-methylbenzene-sulfonate) monohydrate, CAS RN 388082-78-8 and m.p. 250-256° C.

This substance can be prepared following the teachings of the prior art such as for example those contained in U.S. Pat. No. 7,157,466. In examples 10 and 11 this reference shows the preparation of the monohydrate ditosylate salt starting from anhydrous ditosylate salt.

The main disadvantage of such methods, is that some intermediates such as for example those having an aldehyde function in free form are poorly soluble, thus leading to low productivity. In other methods stannane intermediates are used which entail problems related to the disposal of waste water.

SUMMARY OF THE INVENTION

The present invention provides methods for the preparation of Lapatinib and the salts thereof, through a series of new intermediates which overcome or significantly reduce the drawbacks revealed above with reference to the prior art.

Further characteristics and advantages of methods according to the present invention will be apparent from the description.

BRIEF DESCRIPTION OF THE FIGURE

FIG. 1 shows the 1H-NMR spectrum of Lapatinib ditosylate monohydrate obtained according to a presentation method of the present invention.

DETAILED DESCRIPTION OF THE INVENTION

The present invention provides methods for the preparation of Lapatinib of formula (I) or a salt thereof:

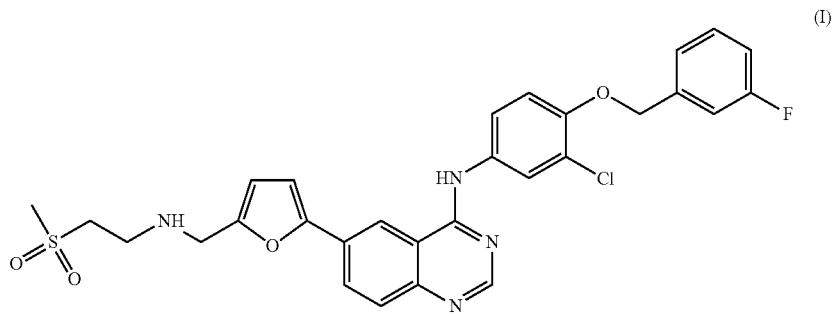 [SMILES: CS(=O)(=O)CCNCc1ccc(-c2ccc3ncnc(Nc4ccc(OCc5cccc(F)c5)c(Cl)c4)c3c2)o1]

(I)

comprising, in certain embodiments, the following steps:

(a) Reaction of 6-iodoquinazoline-4-ol of formula (II):

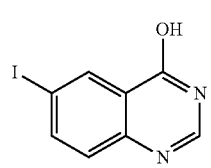
(II)

with 3,4-dihydro-2H-pyran to provide 6-iodo-4-(tetra-hydro-2H-pyran-2-yloxy)quinazoline of formula (III):

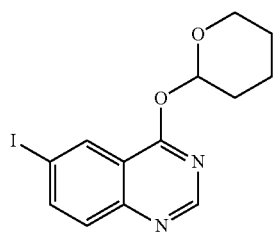
(III)

(b) Reaction of the 6-iodo-4-(tetra-hydro-2H-pyran-2-yloxy)quinazoline of formula (III) with 2-formyl-furan-5-boronic acid to provide 5-[4-(tetrahydro-2H-pyran-2-yloxy)quinazoline-6-yl]furan-2-carbaldehyde of formula (IV):

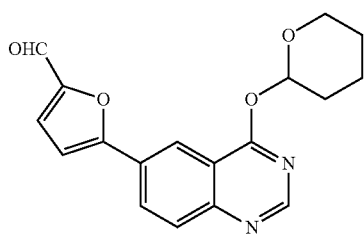
(IV)

(c) Reaction of the intermediate of formula (IV) with 2-(methylsulfonyl)ethanamine to provide 2-(methylsulfonyl)-N-({5-[4-(tetrahydro-2H-pyran-2-yloxy)quinazoline-6-yl]furan-2-yl}methyl) ethanamine of formula (V):

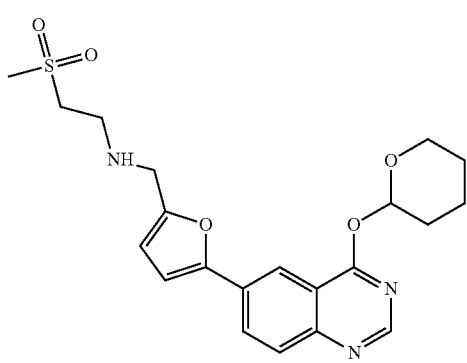
(V)

(d) Reaction of deprotection of the intermediate of formula (V) to provide 6-[5-({[2-(methylsulfonyl)ethyl]amino}methyl)furan-2-yl] quinazoline-4-ol of formula (VI):

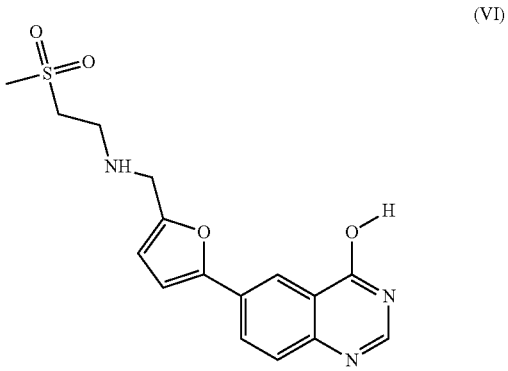 [SMILES: CS(=O)(=O)CCNCc1ccc(-c2ccc3ncnc(O)c3c2)o1]
(VI)

(e) Conversion of the intermediate of formula (VI) to provide N-{[5-(4-substituted-quinazoline-6-yl)furan-2-yl]methyl}-2-(methylsulfonyl) ethanamine of formula (VII):

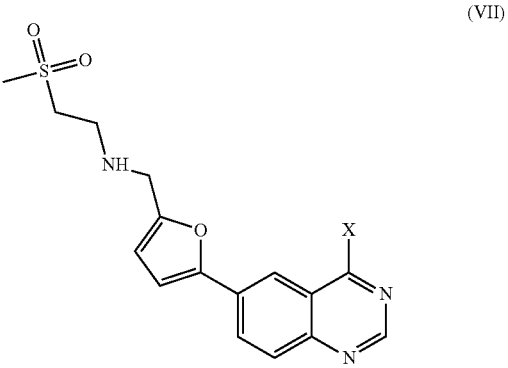
(VII)

wherein X may be fluorine, chlorine, bromine, iodine, O-Ms (mesylate), O-Ts (tosylate), O-If (triflate);

(f) Reaction of the intermediate of formula (VII) with the 3-chloro-4-[(3-fluorobenzyl)oxy]aniline of formula (VIII):

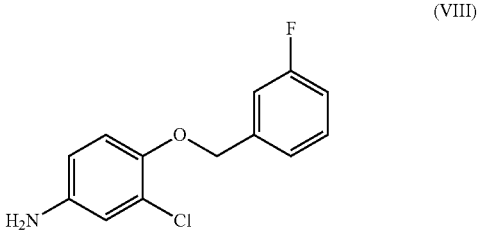 [SMILES: Nc1ccc(OCc2cccc(F)c2)c(Cl)c1]
(VIII)

to provide Lapatinib of formula (I).

(g) Optionally, conversion of the Lapatinib of formula (I) into Lapatinib ditosylate monohydrate.

In certain embodiments, step (a) preparation of the 6-iodo-4-(tetrahydro-2H-pyran-2-yloxy)quinazoline intermediate of formula (III):

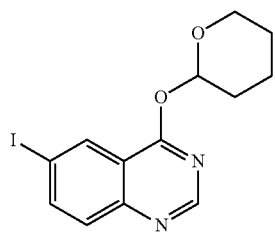

(III)

using tetrahydropyranyl (THP) group starting from 6-iodo-quinazoline-4-ol of formula (II) may be conveniently performed in an organic solvent such as for example Toluene or mixtures such as for example AcOEt/DMF (8:2); this reaction may be performed in toluene. Trifluoroacetic acid in an amount sufficient to catalyze the reaction, may be used. The reaction may be performed at T=110-115° C. (at reflux) for 2-3 hours. The conversion reaction is free of by-products and provides a high yield. The raw product may be purified by means of recrystalisation from 5 volumes of AcOEt, for an overall molar yield of about 73%.

One advantage of this process is that 6-iodo-4-(tetra-hydro-2H-pyran-2-yloxy)quinazoline of formula (III) is more soluble with respect to the initial product allowing continuous operation in the homogeneous phase and the performance possible recrystallizations using small volumes of solvent. Furthermore, the commercial cost of 3,4-dihydro-2H-pyran (DHP) is very low.

In certain embodiments, step (b) preparation of the 5-[4-(tetrahydro-2H-pyran-2-yloxy)quinazoline-6-yl]furan-2-carbaldehyde intermediate of formula (IV):

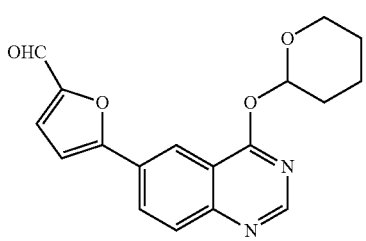

(IV)

through a cross-coupling reaction of the 6-iodo-4-(tetrahydro-2H-pyran-2-yloxy)quinazoline intermediate of formula (III) with 2-formylfuran-5-boronic acid (CAS RN 27329-70-0) may be performed in an organic solvent, such as dimethylformamide in the presence of a palladium tris dibenzylideneacetone and triphenylarsine catalyst system. Other ligands such as triphenylphosphine may be used. The reaction may be performed in the presence of a base, such as for example potassium carbonate. In certain embodiments the reaction is performed in anhydrous conditions and in the absence of oxygen.

Embodiments of the present invention can generate molar yields ranging between 70% and 90%. The product of formula (IV) may be optionally purified by means of pulping from ethyl acetate for an overall molar yield of about 83%. An advantage provided by certain embodiments of the present invention is that the use of 2-formylfuran-5-boronic acid avoids the use of stannanes which are typically used for adding the 2-formylfuran group according to providing known processes regarding this type of coupling, with a clear advantage in terms of toxicity and disposal. 2-formylfuran-5-boronic acid is a readily available substance.

In certain embodiments, step (c) preparation of the 2-(methylsulfonyl)-N-({5-[4-(tetrahydro-2H-pyran-2-yloxy)quinazoline-6-yl]furan-2-yl}methyl)ethanamine intermediate of formula (V):

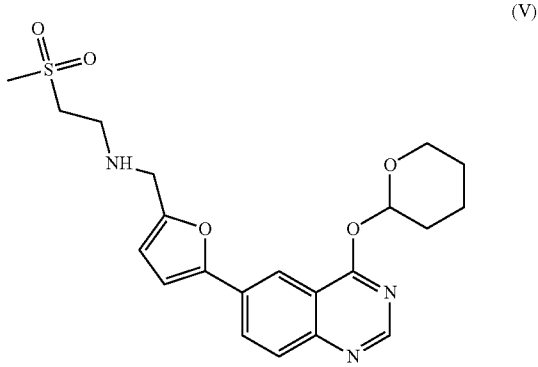 [SMILES: CS(=O)(=O)CCNCc1ccc(-c2ccc3ncnc(OC4CCCCO4)c3c2)o1]

(V)

through the reductive amination reaction of 5-[4-(tetrahydro-2H-pyran-2-yloxy)quinazoline-6-yl]furan-2-carbaldehyde intermediate of formula (IV) with 2-(methylsulfonyl)ethanamine, may be performed in an organic solvent, such as dichloromethane and in the presence of sodium triacetoxyborohydride and Diisopropylethylamine (DIPEA). 2-(methylsulfonyl)ethanamine as a hydrochloride is a product available on the market (CAS RN 104458-24-4).

In certain embodiments the 2-(methylsulfonyl)-N-({5-[4-(tetrahydro-2H-pyran-2-yloxy)quinazoline-6-yl]furan-2-yl}methyl) ethanamine intermediate of formula (V) is an important intermediate since the final product may be obtained therefrom through a number of alternative steps. For example, such intermediate may be directly converted into the N-{[5-(4-bromoquinazoline-6-yl)furan-2-yl]methyl}-2-(methylsulfonyl)ethanamine intermediate of formula (VII, X=Br):

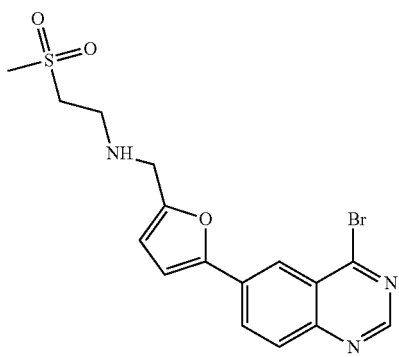

(VII, X = Br)

or into the N-{[5-(4-iodoquinazoline-6-yl)furan-2-yl]methyl}-2-(methylsulfonyl)ethanamine intermediate of formula (VII, X=I):

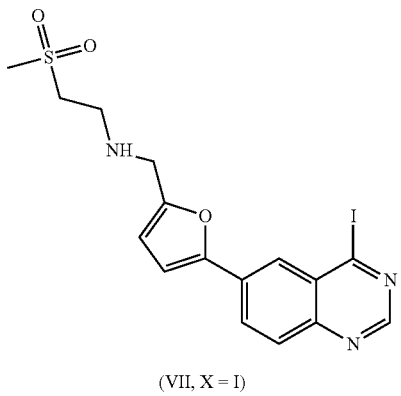 [SMILES: CS(=O)(=O)CCNCc1ccc(-c2ccc3ncnc(I)c3c2)o1]

(VII, X = I)

using, for example, the conditions (LiBr or NaI and BF3.Et2O or trimethylchlorosilane) described by Yashwant D. Vankar et al. in Tetrahedron Letters, vol. 32, n. 8, 1081-1084 (1991) for the direct conversion of tetrahydropyranyl ethers to the corresponding bromides and iodides. Such intermediates of formula (VII, X=Br) and (VII—X=I) may be subjected to the same nucleophilic substitution reaction of the corresponding chlorine derivative of formula (VII) or of the corresponding mesylates of formula (VII) to provide Lapatinib according to step (f).

In certain embodiments, step (d) preparation of the 6-[5-({[2-(methylsulfonyl)ethyl]amino}methyl)furan-2-yl]quinazoline-4-ol intermediate of formula (VI):

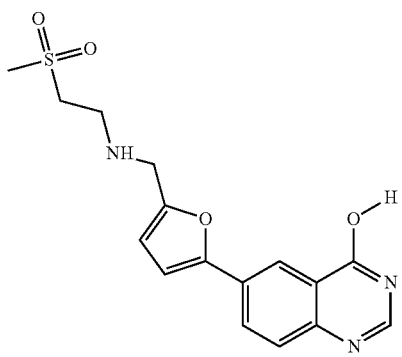

(VI)

through the deprotection of the 2-(methylsulfonyl)-N-({5-[4-(tetrahydro-2H-pyran-2-yloxy)quinazoline-6-yl]furan-2-yl}methyl)ethanamine intermediate of formula (V) may be conveniently performed in alcohol, for example in methanol, in the presence of an acid catalyst such as for example methanesulfonic acid or paratoluenesulfonic acid. The reaction may be performed at ambient temperature for at least 1 hour and is capable of obtaining molar yields around 95%.

In certain embodiments, step (e) preparation of N-{[5-(4-substituted-quinazoline-6-yl)furan-2-yl]methyl}-2-(methylsulfonyl)ethanamine of formula (VII)

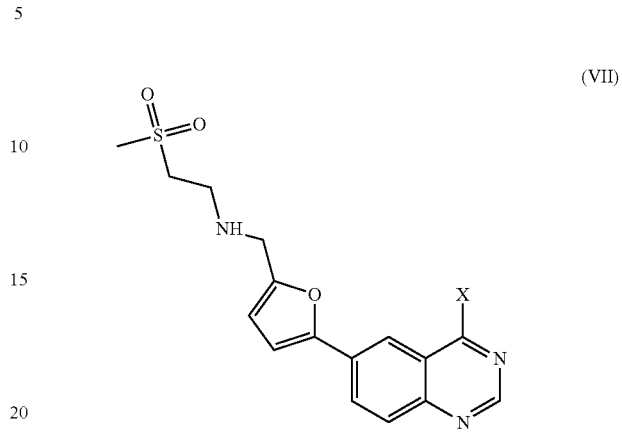

(VII)

may be performed in an organic solvent, such as toluene, by means of halogenation reagents such as for example POCl3, SO2Cl, (COCl)2 and PBr3 or by means of sulfonyl halogenides and sulfonic anhydrides such as for example mesyl chloride, tosyl chloride, tosyl anhydride and triflic anhydride.

In certain embodiments, step (e) preparation of the N-{[5-(4-chloroquinazoline-6-yl)furan-2-yl]methyl}-2-(methylsulfonyl)ethanamine intermediate of formula (VII, X=Cl):

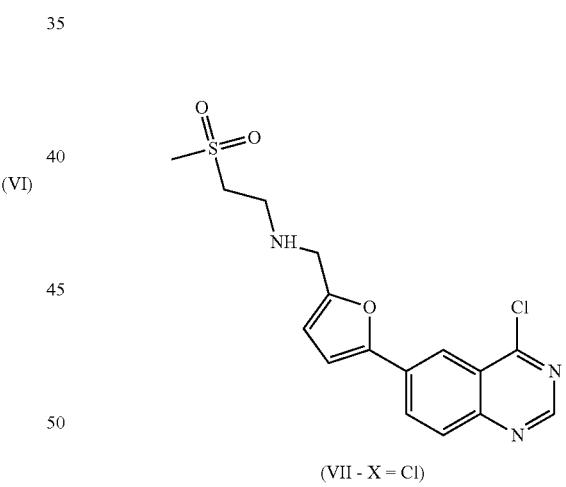

(VII - X = Cl)

through the halogenation of the 6-[5-({[2-(methylsulfonyl)ethyl]amino}methyl)furan-2-yl] quinazoline-4-ol intermediate of formula (VI) may be performed in an organic solvent such as for example toluene by means of phosphoryl oxychloride (POCl3) in the presence of a base such as for example triethylamine (TEA). Other chloride agents such as thionyl chloride or oxalyl chloride may be used. Phosphorus oxychloride may be used in certain embodiments.

In certain embodiments, step (f) preparation of the Lapatinib of formula (I):

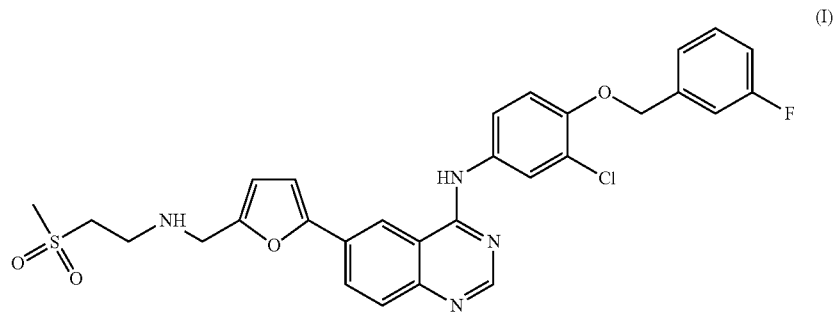 [SMILES: CS(=O)(=O)CCNCc1ccc(-c2ccc3ncnc(Nc4ccc(OCc5cccc(F)c5)c(Cl)c4)c3c2)o1]

(I)

through the coupling reaction of the N-{[5-(4-substituted-quinazoline-6-yl)furan-2-yl]methyl}-2-(methylsulfonyl)ethanamine intermediate of formula (VII) with the 3-chloro-4-[(3-fluorobenzyl)oxy]aniline of formula (VIII):

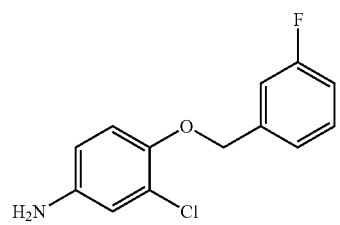

(VIII)

may be conveniently performed in an alcoholic solvent, such as isopropanol and at a temperature between about 60° C. and about 75° C. Should the compound of formula VII have X=Cl, the product may be conveniently isolated directly as a hydrochloric salt. Where X is OTs, the product may be conveniently isolated directly as Lapatinib monotosylate.

In certain embodiments, the step (g) may be performed by first obtaining Lapatinib ditosylate thus subjecting such compound to hydration reaction in water. In certain embodiments, step (g) is not used or is optional.

Intermediate compounds of the present invention having the tetrahydropyranyl group are extremely soluble in organic solvents hence making them particularly useful for industrial application in that they allow the use of much more concentrated solutions with respect to the ones used in the current industrial synthesis of Lapatinib according to the description of U.S. Pat. No. 7,157,466. This allows the production of larger product batch sizes. Methods according to the present invention provide high productivity thus leading to a considerable reduction of the Lapatinib industrial production costs.

EXAMPLES

Example 1

Preparation of the Intermediate 6-iodo-4-(tetrahydro-2H-pyran-2-yloxy)quinazoline of Formula (III)

Synthesis scheme

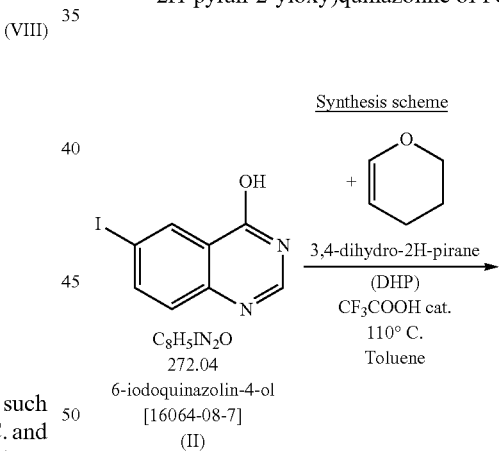

$C_8H_5IN_2O$
272.04
6-iodoquinazolin-4-ol
[16064-08-7]
(II)

3,4-dihydro-2H-pirane
(DHP)
$CF_3COOH$ cat.
110° C.
Toluene

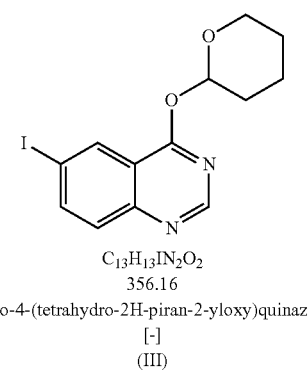

$C_{13}H_{13}IN_2O_2$
356.16
6-iodo-4-(tetrahydro-2H-piran-2-yloxy)quinazoline
[-]
(III)

In a 4-neck glass flask provided with a mechanical stirrer, condenser and thermometer 30 g of 6-iodoquinazoline-4-ol (110 mmoles), 300 mL of toluene dried on molecular sieves, 1.26 g (0.84 mL) of trifluoroacetic acid (0.1 mol. equiv.) and 79.4 g (80 mL) of 3,4-dihydro-2H-pyran (DHP) (944 mmoles; 8.6 mol. equiv.) were introduced, under nitrogen. Stirring was carried out to reflux (T=110-115° C.) for 2-3 hours and the reaction was controlled under TLC with Hexane/Ethyl Acetate (2:8) eluent. Upon completing the reaction a homogeneous solution was obtained which was cooled to ambient temperature and washed using 2×120 mL of saturated solution of sodium chloride. The organic phase was concentrated under vacuum to 40-45° C. ext T up to residue.

The product was recrystalised by adding 150 mL of Ethyl acetate and heating to reflux. Cooling was carried out up to ambient temperature and stirring was carried out for 30 minutes then cooling was carried out at 0-5° C. and stirring was carried out for 30 minutes. The suspension was filtered and the solid was washed with 60 mL of ethyl acetate pre-cooled at 0-5° C. The product was dried under vacuum at 40° C. for 6-8 hours obtaining 28.6 g of the product as a white crystalline solid for a molar yield equivalent to 72.8%.

1H-NMR (400 MHz, DMSO-d6): 1.75 (m, 6H, CH2 (THP)); 3.69 (dt, J=11.6, 2.9 Hz, 1H, CH2O(THP)); 4.11 (app. d, J=11.6 Hz, 1 H, CH2O(THP)); 5.85 (dd, J=8.7, 4.2 Hz, 1H, O—CHO(THP)); 7.50 (d, J=8.5 Hz, 1 H, H-8); 8.16 (dd, J=8.5, 1.5 Hz, 1H, H-7); 8.45 (d, J=1.8 Hz, 1H, H-5); 8.45 (s, 1H, H-2).

Example 2

Preparation of the 5-[4-(tetrahydro-2H-pyran-2-yloxy)quinazoline-6-yl]furan-2-carbaldehyde Intermediate of Formula (IV)

Synthesis scheme

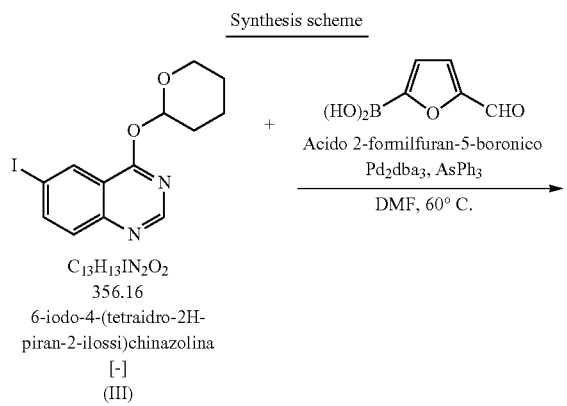

$C_{13}H_{13}IN_2O_2$
356.16
6-iodo-4-(tetraidro-2H-piran-2-ilossi)chinazolina
[-]
(III)

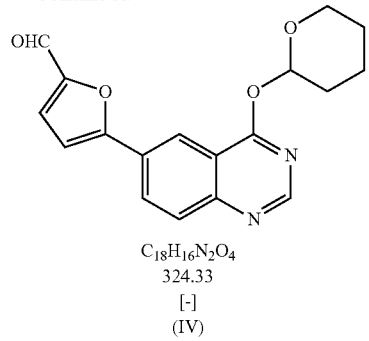

$C_{18}H_{16}N_2O_4$
324.33
[-]
(IV)

Acido 2-formilfuran-5-boronico = 2-formylfuran-5-boronic acid
6-iodo-4-(tetraedro-2H-piran-2-ilossi)chinazolina = 6-Iodo-4-(tetrahydro-2H-pyran-2-yloxy) quinazoline In a 4-neck glass flask provided with a mechanical stirrer, condenser and thermometer, the entirety having been previously dried, 320 mg of palladium tris dibenzylideneacetone (Johnson-Mattey—Pd-94; 1.25% mol.) weighed under nitrogen and 430 mg of triphenylarsine (Aldrich) (0.025 mol. equiv.) were introduced, under nitrogen atmosphere. 200 mL of previously degassed anhydrous DMF was added under nitrogen for 1 hour. Stirring was carried out for 10-15 minutes at ambient temperature followed by the addition of 15.5 g of potassium carbonate (2 mol. equiv.) and 10.2 g of 2-formylfuran-5-boronic acid (1.3 mol. equiv.) and lastly 20.0 g of 6-iodo-4-(tetrahydro-2H-pyran-2-yloxy)quinazoline of formula (III). The reaction mixture was heated for 2 hours at 60-65° C. The reaction may be controlled by means of TLC using Hexane/AcOEt (6:4) as eluent.

Upon completing the reaction 200 mL of purified water was added and extraction carried out with 2×500 mL of dichloromethane. The phases were separated and the aqueous phase was washed with 2×300 mL of NaHCO3 at 5%, then with 2×300 mL of a saturated solution of sodium chloride. The organic phase was then dried with anhydrous sodium sulfate then with 2.0 g of Acticarbone and filtered on a dicalite panel which was then washed with 2×100 mL of dichloromethane. The solution was washed, concentrated to residue under vacuum at 35-40° C. ext T. The residue, a yellow/orange solid, was recovered using 200 mL of AcOEt.

The stirring was carried out at 20-25° C. for 30 minutes and then cooling was carried out at 0-5° C. Stirring was carried out for another 30 minutes. The suspension was filtered and the solid washed with 80 mL of AcOEt pre-cooled at 0-5° C. The solid was dried in an oven at 35-40° C. for 4-5 hours. 13.5 g of product was obtained for a molar yield equivalent of 74.1%.

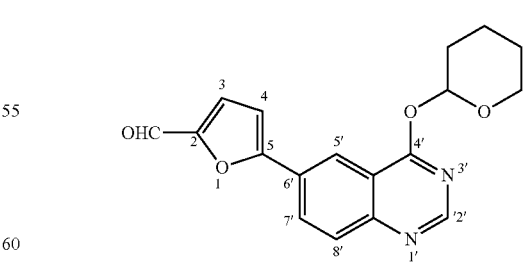

1H NMR (400 MHz, DMSO-d6): 1.77 (m, 6H, CH2 (THP)); 3.73 (dt, J=11.6, 2.7 Hz, 1H, CH2O(THP)); 4.13 (app. dd, J=11.0, 1.6 Hz, 1 H, CH2O(THP)); 5.90 (dd, J=8.2, 4.6 Hz, 1H, OCHO(THP)); 7.53 (d, J=3.7 Hz, 1 H, CH(furan)); 7.72 (d, J=3.7 Hz, 1 H, CH(furan)); 7.84 (d, J=8.6 Hz, 1H, H-8'); 8.48 (dd, J=8.5, 1.9 Hz, 1H,H-7'); 8.51 (s, 1H, H-2'); 8.59 (d, J=1.6 Hz, 1H, H-5'); 9.68 (s, 1H, CHO).

Example 3

Preparation of the 2-(methylsulfonyl)-N-({5-[4-(tetrahydro-2H-pyran-2-yloxy)quinazoline-6-yl]furan-2-yl}methyl)ethanamine Intermediate of Formula (V)

Synthesis scheme

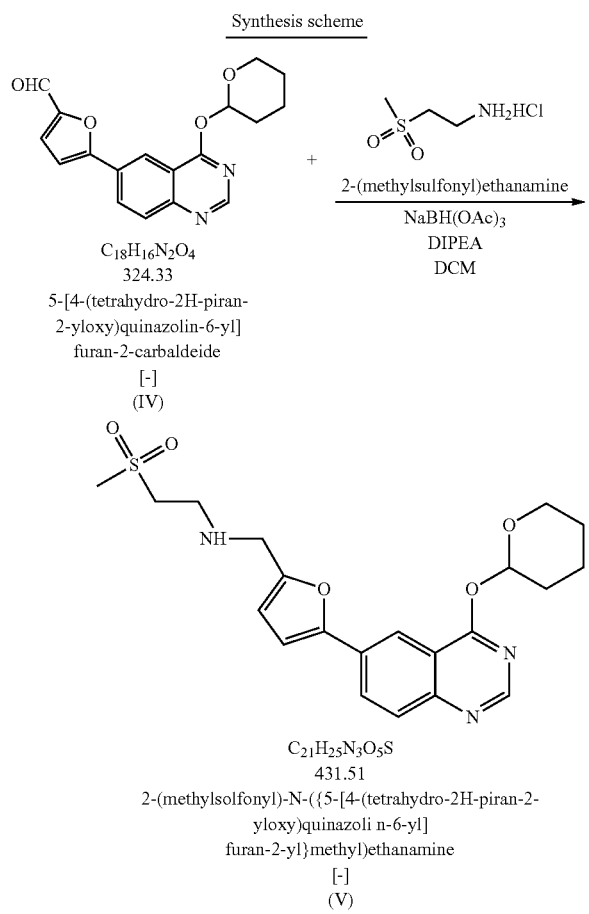

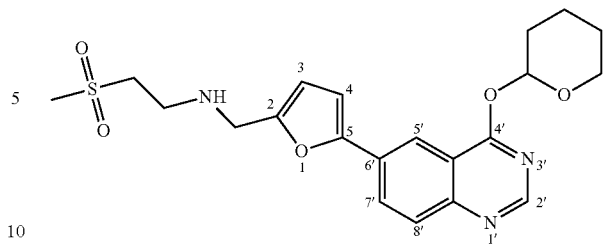

1H NMR (400 MHz, DMSO-d6): 1.86 (m, 6H, CH2 (THP)); 2.99 (t, J=6.6 Hz, 2 H, —SO2CH2CH2NH—); 3.05 (s, 3 H, CH3); 3.28 (t, J=6.6 Hz, 2 H, —SO2CH2CH2NH—); 3.71 (dt, J=11.8, 2.9 Hz, 1H, CH2O(THP)); 3.83 (s, 2 H, —NH—CH2-furan); 4.12 (app. d, J=11.0, 1 H, CH2O (THP)); 5.90 (dd, J=8.8, 4.4 Hz, 1H, OCHO(THP)); 6.46 (d, J=3.2 Hz, 1 H, CH(furan)); 7.10 (d, J=3.2 Hz, 1 H, CH(furan)); 7.74 (d, J=8.6 Hz, 1H, H-8'); 8.17 (dd, J=8.5, 2.0 Hz, 1H, H-7'); 8.38 (d, J=1.8 Hz, 1H, H-5'); 8.43 (s, 1H, H-2').

Example 4

Preparation of the Intermediate 6-[5-({[2-(methylsulfonyl)ethyl]amino}methyl)furan-2-yl] quinazoline-4-ol of Formula (VI)

Synthesis scheme

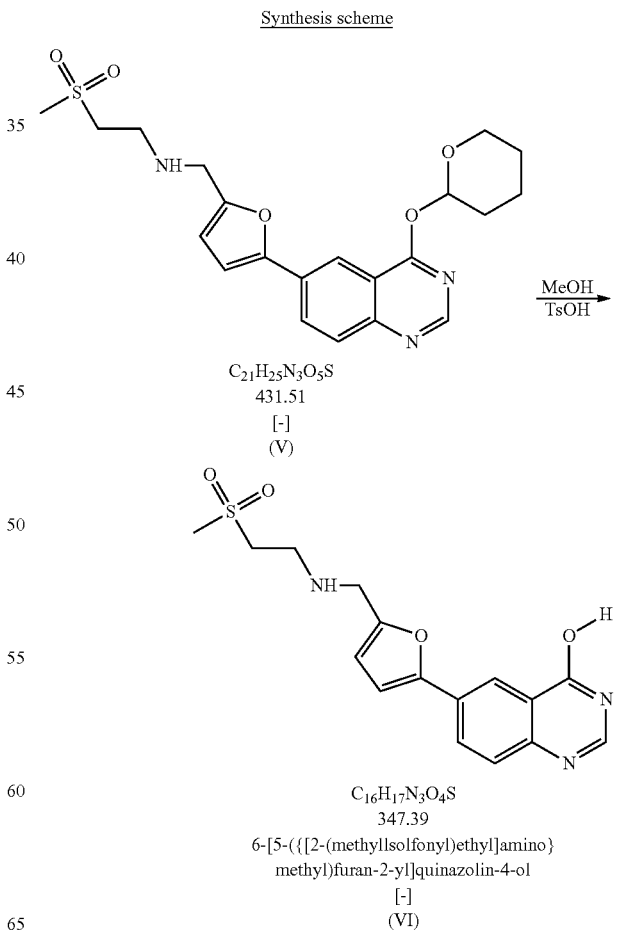

In a 4-neck glass flask provided with a mechanical stirrer, condenser and thermometer, the entirety having been previously dried, 1.0 g of 5-[4-(tetrahydro-2H-pyran-2-yloxy) quinazoline-6-yl]furan-2-carbaldehyde of formula (IV) and 20 mL of anhydrous dichloromethane were introduced, under nitrogen atmosphere. There were added, at 20-25° C., 0.73 g of 2-(methylsulfonyl)ethanamine hydrochloride (1.5 mol. equiv.) and 0.60 g (0.80 mL) of diisopropylethylamine (DIPEA) (1.5 mol. equiv.). Stirring was carried out for 30 minutes at 30-35° C. Cooling was carried out at 20-25° C. and 1.31 g of triacetoxy sodium borohydride (Aldrich) (2.0 mol. equiv.) were added. Stirring was carried out at 20-25° C. for 2 hours then the conversion was controlled under TLC using the Hexane/Ethyl acetate 6:4 mixture as eluent. Upon completing the reaction 10 mL of a saturated solution of sodium bicarbonate are added, the phases separated and the organic phase was dried on anhydrous sodium sulphate, whereupon it was concentrated under vacuum at 35-40° C. ext T up to residue. The product was dried by means of high vacuum (using an Edwards pump). 1.06 g of product was obtained for a molar yield equivalent to about 80%.

In a 4-neck glass flask provided with a mechanical stirrer, condenser and thermometer, the entirety having been previously dried, 1.0 g of 2-(methylsulfonyl)-N-({5-[4-(tetrahydro-2H-pyran-2-yloxy)quinazoline-6-yl]furan-2-yl}methyl)ethanamine of formula (V), 20 mL of methanol and 0.5 g of paratoluenesulfonic acid were introduced. The product was left under stirring at 25° C. for at least 1 hour. Upon completing the reaction there were added 50 mL of AcOEt and 50 mL of 5% aqueous NaHCO3. The phases were separated. The organic phase was concentrated to residue under low pressure and 35° C. ext T. 0.76 g of product was obtained with a 95% molar yield.

Example 5

Preparation of the Intermediate N-{[5-(4-chloroquinazoline-6-yl)furan-2-yl]methyl}-2-(methylsulfonyl)ethanamine of Formula (VII)

Synthesis scheme

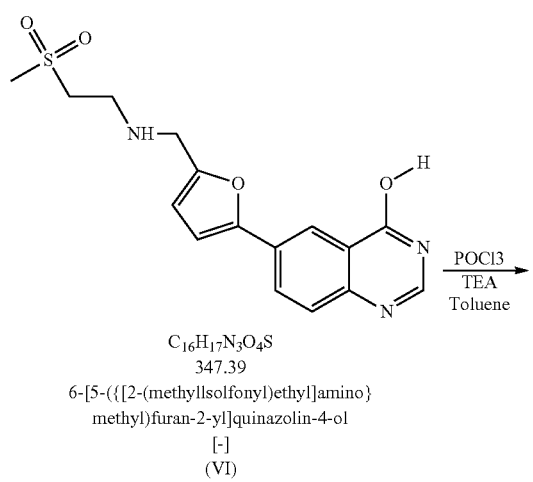

$C_{16}H_{17}N_3O_4S$
347.39
6-[5-({[2-(methyllsolfonyl)ethyl]amino}methyl)furan-2-yl]quinazolin-4-ol
[-]
(VI)

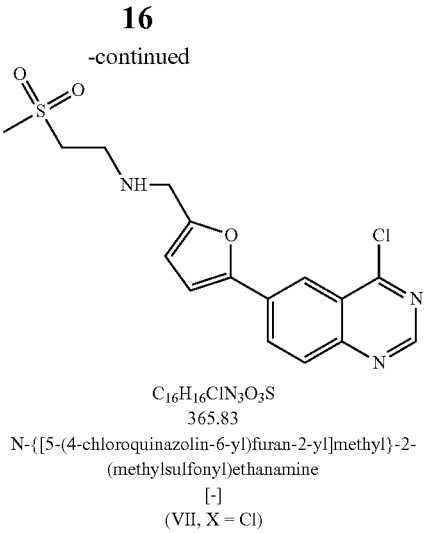

$C_{16}H_{16}ClN_3O_3S$
365.83
N-{[5-(4-chloroquinazolin-6-yl)furan-2-yl]methyl}-2-(methylsulfonyl)ethanamine
[-]
(VII, X = Cl)

In a 4-neck glass flask provided with a mechanical stirrer, condenser and thermometer, the entirety having been previously dried, 63.8 g of 6-[5-({[2-(methylsulfonyl)ethyl]amino}methyl)furan-2-yl] quinazoline-4-ol of formula (VI) (0.184 moles), 33.7 g (20.1 mL) of phosphoryl oxychloride (POCl3; 0.220 moles) and 150 mL of toluene were introduced, under nitrogen. Stirring was carried out at ambient temperature for 10 minutes then 22.3 g (30.7 mL) of triethylamine (0.220 moles) was dosed, maintaining the T below 30° C. After introduction heating was carried out at 75° C. for 3 hours. The reaction was controlled by means of TLC using the Hexane/Ethyl acetate mixture (4:6) as eluent. Cooling was carried out at 0° C. and stirring was carried out for an hour at such temperature. The suspension was filtered washing the solid with 100 mL of toluene. The product was dried at 50° C. for 7-8 hours under vacuum. 63.8 g of product was added with a molar yield equivalent to 95%.

Example 6

Preparation of Lapatinib of Formula (I) as a Hydrochloride Salt

Synthesis scheme

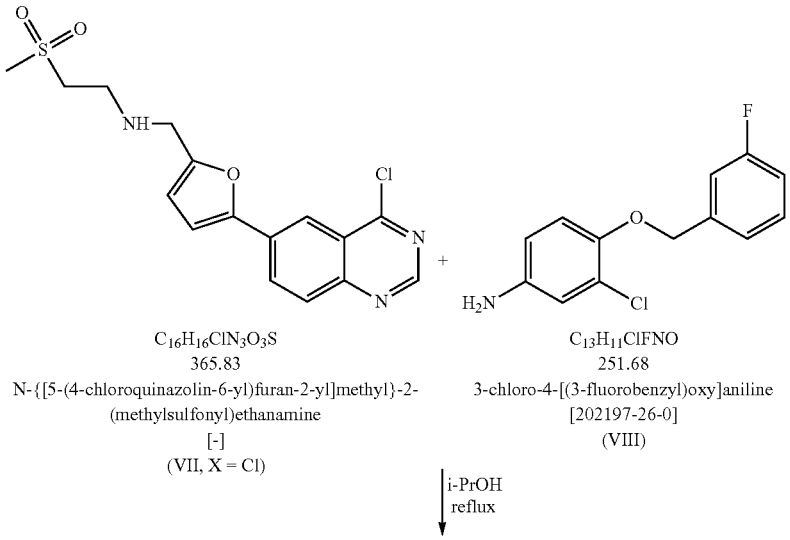

$C_{16}H_{16}ClN_3O_3S$
365.83
N-{[5-(4-chloroquinazolin-6-yl)furan-2-yl]methyl}-2-(methylsulfonyl)ethanamine
[-]
(VII, X = Cl)

$C_{13}H_{11}ClFNO$
251.68
3-chloro-4-[(3-fluorobenzyl)oxy]aniline
[202197-26-0]
(VIII)

i-PrOH reflux

-continued

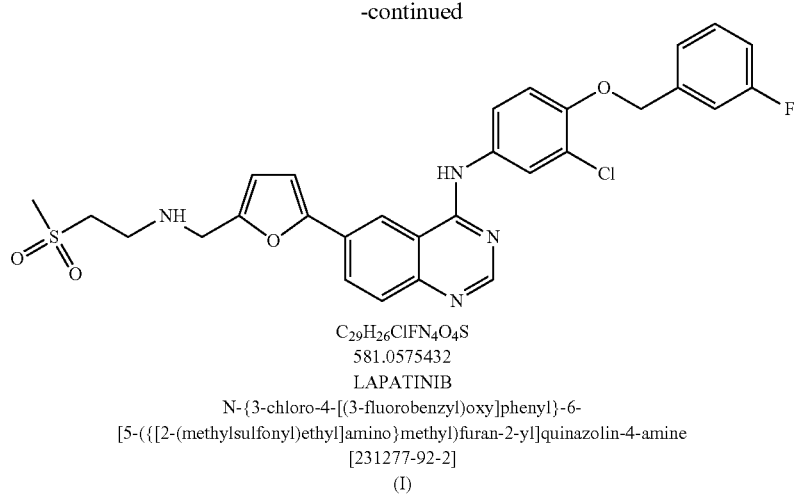

C₂₉H₂₆ClFN₄O₄S
581.0575432
LAPATINIB
N-{3-chloro-4-[(3-fluorobenzyl)oxy]phenyl}-6-
[5-({[2-(methylsulfonyl)ethyl]amino}methyl)furan-2-yl]quinazolin-4-amine
[231277-92-2]
(I)

In a 4-neck glass flask provided with a mechanical stirrer, condenser and thermometer, the entirety having been previously dried, 10.0 g of 3-chloro-4-[(3-fluoro-benzyl)oxy] aniline of formula (VIII) (39.7 mmoles), 14.6 g of N-{[5-(4-chloroquinazoline-6-yl)furan-2-yl]methyl}-2-(methylsulfonyl)ethanamine of formula (VII) (40.0 mmoles, 1.005 mol. equiv.) and 200 mL of isopropanol were introduced, under nitrogen.

Stirring was carried out at 70° C. for 4 hours. Upon completing the reaction, cooling was carried out at ambient temperature. It is left under stirring for 1 hour. The solid was filtered and washed with 14 mL of cold isopropanol. It was dried under vacuum at 40° C. for 4-6 hours. 23.5 g of product was obtained with a molar yield equivalent to 96%.

Example 7

Preparation of Lapatinib of Formula (I) as a Ditosylate Salt

In a 4-neck glass flask provided with a mechanical stirrer, condenser and thermometer, 9.70 g of Lapatinib chloro-hydrate (15.7 mmoles), 120 ml of ethyl acetate and 25 mL of purified water were introduced under nitrogen.

About 4.6 g of NaOH 30% solution (p/p) were dripped up to a pH of about 10. The phases were separated and the organic phase was washed with 2×30 mL of purified water. The organic phase was concentrated under vacuum to dryness.

The residue was recovered using 28 mL of dimethylformamide. Heating was carried out at 40° C. for 15 minutes and filtration was carried out on a dicalite panel. The panel was washed with 21 ml of dimethylformamide pre-heated at 50° C. The organic phases were combined and brought to 40° C. They were added portionwise with 6.74 g of paratoluenesulfonic acid monohydrate (2.25 mol. equiv.). Stirring was carried out at 40° C. for 1 hour and then cooling was carried out within 3-4 hours at 0° C. 0.08 g of Lapatinib ditosylate were added to initiate the precipitation and stirring was carried out for 4 hours at 0° C., then cooling was carried out at −10° C. and stirring was carried out for 2 hours. The suspension was filtered and the solid was washed with 4.8 mL of dimethylformamide pre-cooled to −10° C. The product was dried under vacuum at 70° C. for at least 10 hours. 13.1 g of product were obtained with a molar yield equivalent to 90.1%.

Example 8

Preparation of Lapatinib Ditosylate Monohydrate Formula (I-bis)

In a 4-neck glass flask provided with a mechanical stirrer, condenser and thermometer, 50.0 g of Lapatinib ditosylate and 500 mL of water were introduced under nitrogen. Stirring was carried out for 36 hours at ambient temperature. Filtration was carried out draining the product thoroughly and the product was washed using the mother liquors. The product was dried at ambient temperature under the flow of nitrogen in a flask provided with a stirrer.

The product was thus dried for 24 hours at 55° C. up to K.F. around 1.92%. 51 g of product were obtained for a quantitative molar yield.

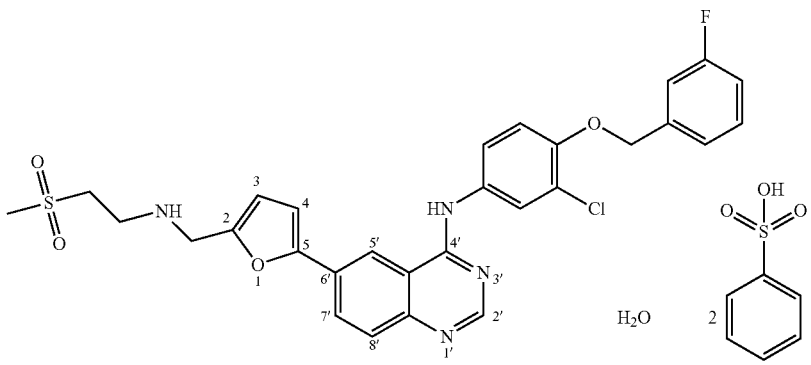

1H NMR (400 MHz, DMSO-d6): 2.31 (s, 6 H, CH3 (TsOH)); 3.17 (s, 3 H, CH3SO2); 3.50-3.65 (m, 4 H, —SO2CH2CH2NH—); 4.52 (s, 2, NH—CH2-furan); 5.35 (s, 2 H, ArO—CH2-Ar); 6.93 (d, J=3.4 Hz, 1 H, CH(furan)); 7.14 (d, J=7.8 Hz, 4 H, CH(TsOH)); 7.24 (dt, J=8.8, 2.1 Hz, 1 H, Ar); 7.32 (d, J=3.4 Hz, 1 H, CH(furan)); 7.53 (d, J=8.0 Hz, 4 H, CH(TsOH)); 7.65 (dd, J=8.9, 2.5 Hz, Ar); 7.90 (d, J=2.6 Hz, 1H, H-5'); 7.97 (d, J=8.8 Hz, 1 H, H-8'); 8.48 (dd, J=8.8, 1.5 Hz, 1 H, H-7'); 8.99 (s, 1 H, H-2'); 9.10 (s, 1 H, Ar); 9.40 (br. s, 1 H, NH); 11.48 (s, 1 H, NH).

Example 9

Preparation of N-{[5-(4-bromoquinazoline-6-yl)furan-2-yl]methyl}-2-(methylsulfonyl)ethanamine of Formula (VII, X=Br) (Variant)

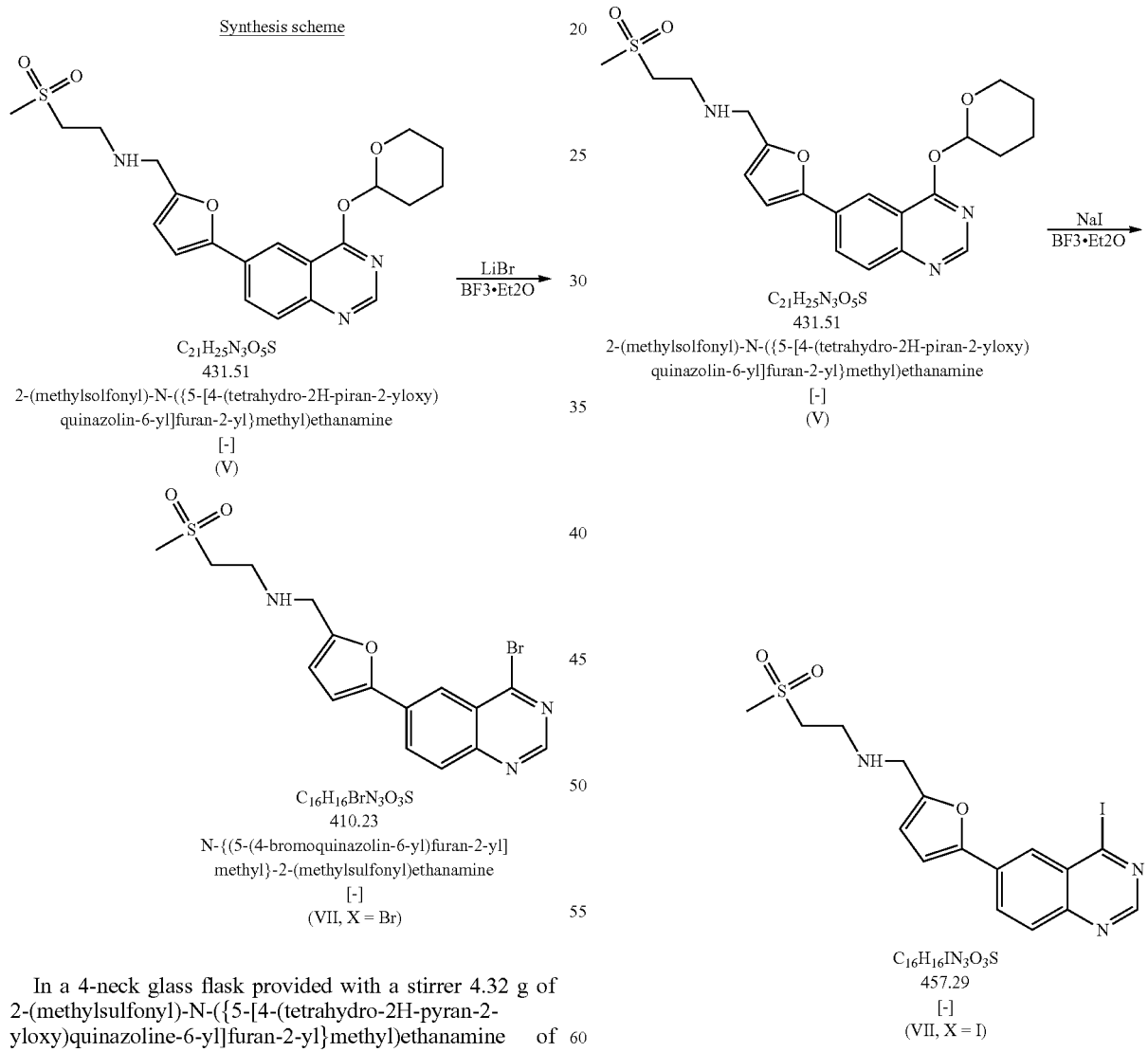

In a 4-neck glass flask provided with a stirrer 4.32 g of 2-(methylsulfonyl)-N-({5-[4-(tetrahydro-2H-pyran-2-yloxy)quinazoline-6-yl]furan-2-yl}methyl)ethanamine of formula (V) (10 mmoles), 0.87 g of LiBr (10 mmoles) and 10 mL of acetonitrile were introduced. Under a nitrogen atmosphere and maintaining the temperature at about 0° C. there were added 1.56 g of freshly distilled BF3.Et2O (11 mmoles). The mixture was brought to ambient temperature and stirred for 24 hours. The mixture was thus concentrated to residue and the residue was recovered using 200 mL of ether. The solution was washed using a 10% sodium thiosulfate solution, then using water, then using brine. The organic phase was dried using anhydrous Na2SO4 then concentrated to residue. 3.08 g of N-{[5-(4-bromoquinazoline-6-yl)furan-2-yl]methyl}-2-(methylsulfonyl)ethanamine of formula (VII, X=Br) were obtained with a molar yield equivalent to 75%.

Example 10

Preparation of N-{[5-(4-iodoquinazoline-6-yl)furan-2-yl]methyl}-2-(methylsulfonyl)ethanamine of Formula (VII, X=I) (Variant)

The process was repeated as in Example 9 where 1.50 g of sodium iodide (NaI, 10 mmoles) were used instead of LiBr. 3.2 g of N-{[5-(4-iodoquinazoline-6-yl)furan-2-yl]methyl}-2-(methylsulfonyl)ethanamine of formula (VII, X=I) were obtained with a molar yield equivalent to 70%.

The invention claimed is:

1. A method for the preparation of Lapatinib of formula (I) or a salt thereof:

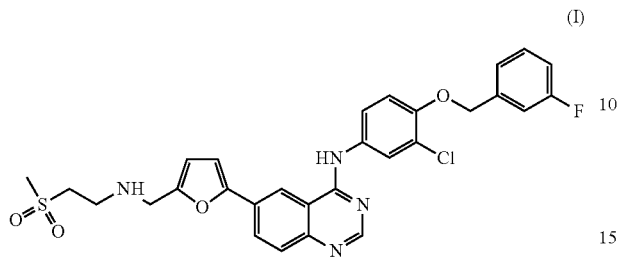
(I)

comprising the steps of:

(a) reacting of 6-iodoquinazolin-4-ol of formula (II):

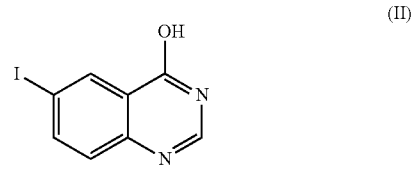 [SMILES: Oc1ncnc2ccc(I)cc12]
(II)

with 3,4-dihydro-2H-pyran to provide 6-iodo-4-(tetrahydro-2H-pyran-2-yloxy)quinazoline of formula (III):

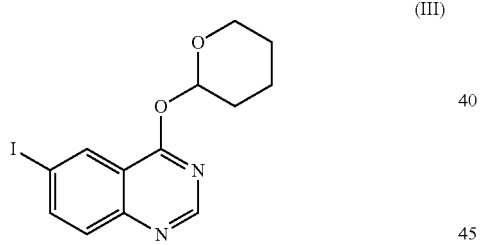
(III)

(b) reacting of 6-iodo-4-(tetrahydro-2H-pyran-2-yloxy) quinazoline of formula (III) with 2-formylfuran-5-boronic acid to provide 5-[4-(tetrahydro-2H-pyran-2-yloxy)quinazolin-6-yl]furan-2-carbaldehyde of formula (IV):

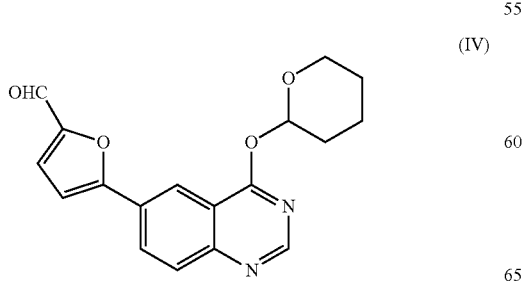
(IV)

(c) reacting of the intermediate of formula (IV) with 2-(methylsulfonyl)ethanamine to provide 2-(methylsulfonyl)-N-({5-[4-(tetrahydro-2H-pyran-2-yloxy)quinazolin-6-yl]furan-2-yl}methyl)ethanamine of formula (V):

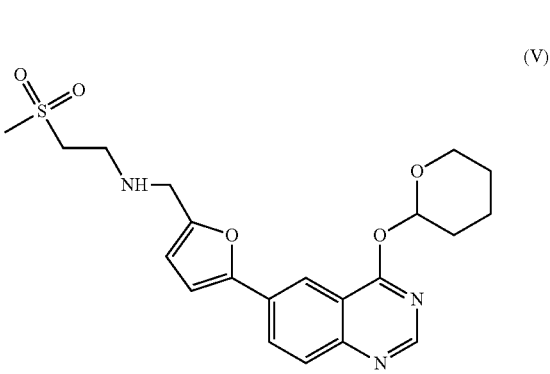 [SMILES: CS(=O)(=O)CCNCc1ccc(-c2ccc3ncnc(OC4CCCCO4)c3c2)o1]
(V)

(d) deprotecting of the intermediate of formula (V) to provide 6-[5-({[2-(methylsulfonyl)ethyl]amino}methyl) furan-2-yl] quinazolin-4-ol of formula (VI):

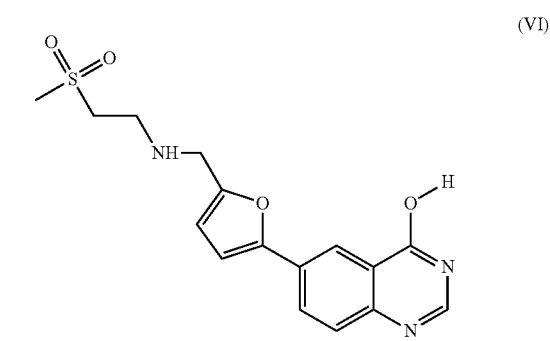 [SMILES: CS(=O)(=O)CCNCc1ccc(-c2ccc3ncnc(O)c3c2)o1]
(VI)

(e) converting of the intermediate of formula (VI) to provide N-{[5-(4-substituted-quinazolin-6-yl)furan-2-yl] methyl}-2-(methylsulfonyl) ethanamine of formula (VII):

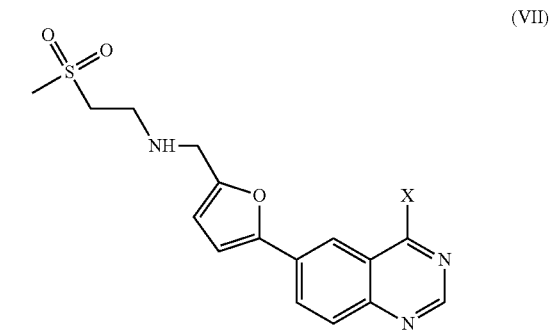
(VII)

in which X is selected from the group consisting of: fluorine, chlorine, bromine, iodine, O-Ms (mesilate), and O-Ts (tosilate), O-Tf (triflate);

(f) reacting of the intermediate of formula (VII) with 3-chloro-4-[(3-fluorobenzyl)oxy]aniline of formula (VIII):

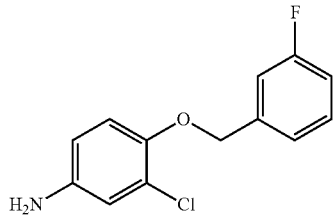

(VIII)

to provide Lapatinib of formula (I):

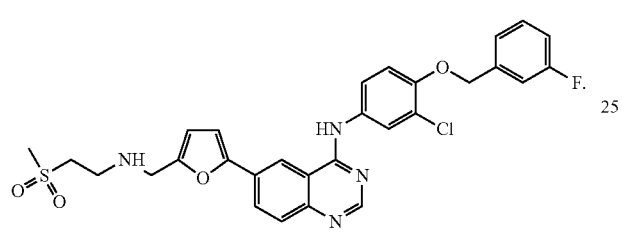

(I)

2. A method for the preparation of 2-(methylsulfonyl)-N-({5-[4-(tetrahydro-2H-pyran-2-yloxy)quinazolin-6-yl]furan-2-yl}methyl)ethanamine of formula (V) or a salt thereof:

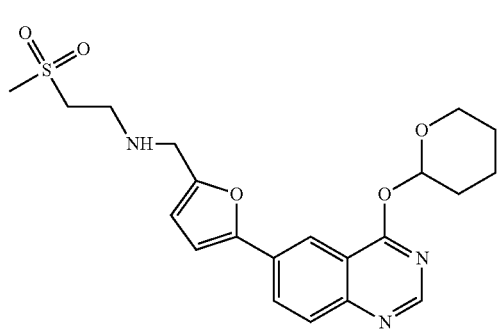

(V)

comprising the steps of:
(a) reacting 6-iodoquinazolin-4-ol of formula (II):

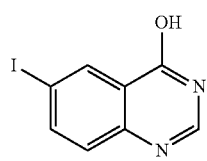

(II)

with 3,4-dihydro-2H-pyran to provide 6-iodo-4-(tetrahydro-2H-pyran-2-yloxy)quinazoline of formula (III):

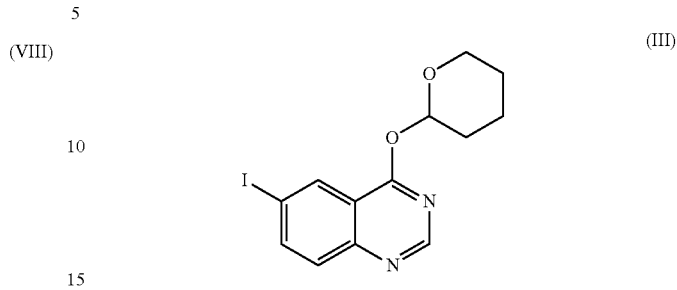

(III)

(b) reacting of 6-iodo-4-(tetrahydro-2H-pyran-2-yloxy) quinazoline of formula (III) with -2-formylfuran-5-boronic acid to provide 5-[4-(tetrahydro-2H-pyran-2-yloxy)quinazolin-6-yl]furan-2-carbaldehyde of formula (IV):

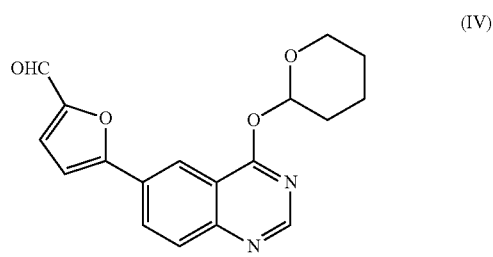 [SMILES: O=Cc1ccc(-c2ccc3ncnc(OC4CCCCO4)c3c2)o1]

(IV)

and (c) reacting of the intermediate of formula (IV) with 2-(methylsulfonyl)ethanamine.

3. The method of claim 1 in which the step (a) is performed in toluene.

4. The method of claim 2 in which the step (a) is performed in toluene.

5. The method of claim 1 in which the step (a) comprises the recrystallization of the product of formula (III) from ethyl acetate.

6. The method of claim 1 in which the step (b) is performed in anhydrous conditions and in the absence of oxygen.

7. The method of claim 1 in which the step (b) is performed in the presence of palladium tris dibenzylydeneacetone.

8. The method of claim 1 in which the step (c) is performed in the presence of sodium triacetoxyborohydride.

9. The method of claim 1 in which the step (d) is performed in an alcoholic solvent.

10. The method of claim 1 in which the step (e) is performed in the presence of phosphorus oxychloride.

11. The method of claim 1 in which the product of the step (e) is N-{[5-(4-Chloro-quinazolin-6-yl)furan-2-yl]methyl}-2-(methylsulfonyl)ethanamine of formula (VII, X═Cl):

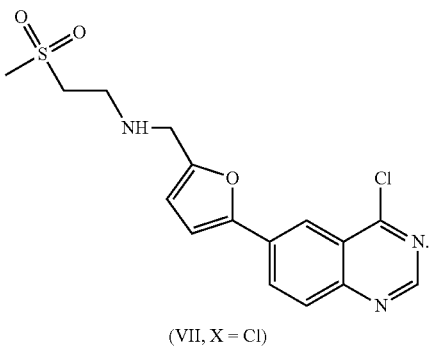 [SMILES: CS(=O)(=O)CCNCc1ccc(-c2ccc3ncnc(Cl)c3c2)o1]

(VII, X = Cl)

12. The method of claim 1 in which the step (f) is performed in isopropanol.

13. The method of claim 1 in which steps (d) and (e) are replaced by the reaction of 2-(methylsulfonyl)-N-({5-[4-(tetrahydro-2H-pyran-2-yloxy)quinazoline-6-yl]furan-2-yl}methyl)ethanamine of formula (V) with LiBr or NaI and BF$_3$.ET$_2$O or trimethylchlorosilane to give N-{[5-(4-bromoquinazoline-6-yl)furan-2-yl]methyl}-2-(methylsulfonyl) ethanamine of formula (VII, X=Br) or N-{[5-(4-iodoquinazoline-6-yl)furan-2-yl]methyl}-2-(methylsulfonyl) ethanamine of formula (VII, X=I), respectively.

14. A compound selected from the group consisting of:
(a) 6-iodo-4-(tetrahydro-2H-pyran-2-yloxy)quinazoline of formula (III),
(b) 5-[4-(tetrahydro-2H-pyran-2-yloxy)quinazolin-6-yl] furan-2-carbaldehyde of formula (IV),
(c) 2-(methylsulfonyl)-N-({5-[4-(tetrahydro-2H-pyran-2-yloxy)quinazolin-6-yl]furan-2-yl}methyl) ethanamine of formula (V),
(d) N-{[5-(4-substituted-quinazolin-6-yl)furan-2-yl]methyl}-2-(methylsulfonyl)ethanamine of formula (VII):

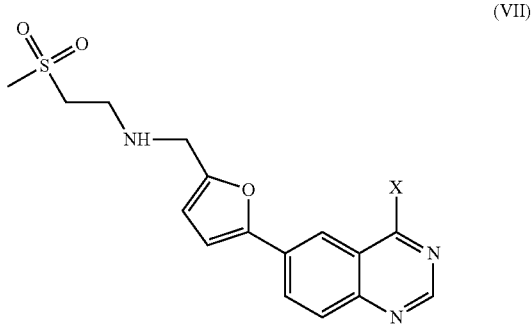

(VII)

in which X may be O-Ms (mesilate), O-Ts (tosilate), or O-Tf (triflate); or a salt thereof.

* * * * *